United States Patent [19]
Noda

[11] Patent Number: 5,336,229
[45] Date of Patent: Aug. 9, 1994

[54] DUAL LIGATING AND DIVIDING APPARATUS

[75] Inventor: Wayne A. Noda, Mission Viejo, Calif.

[73] Assignee: Laparomed Corporation, Irvine, Calif.

[21] Appl. No.: 15,220

[22] Filed: Feb. 9, 1993

[51] Int. Cl.⁵ ............................................. A61B 17/00
[52] U.S. Cl. .................................. 606/144; 606/139; 606/148; 606/170
[58] Field of Search ............... 606/41, 49, 139, 144, 606/145, 148, 151, 165, 170

[56] References Cited

U.S. PATENT DOCUMENTS

| | | | |
|---|---|---|---|
| 1,933,024 | 10/1933 | Nagelmann | 606/145 |
| 3,006,344 | 10/1961 | Vogelfanger . | |
| 3,040,747 | 6/1962 | Wood | 606/139 |
| 3,175,556 | 3/1965 | Wood et al. . | |
| 3,545,444 | 12/1970 | Green . | |
| 3,584,628 | 6/1971 | Green . | |
| 3,608,544 | 9/1971 | Schnepper . | |
| 3,665,924 | 5/1972 | Noiles et al. . | |
| 3,675,688 | 7/1972 | Bryan et al. . | |
| 3,735,762 | 5/1973 | Bryan et al. . | |
| 4,086,926 | 5/1978 | Green et al. . | |
| 4,513,746 | 4/1985 | Aranyi et al. . | |
| 5,037,433 | 8/1991 | Wick et al. | 606/144 |
| 5,129,912 | 7/1992 | Noda et al. | 606/139 |
| 5,147,373 | 9/1992 | Ferzli | 606/144 |
| 5,176,695 | 1/1993 | Dulebohn | 606/170 |
| 5,196,022 | 3/1993 | Bilweis | 606/144 |

FOREIGN PATENT DOCUMENTS 0912619  5/1954  Fed. Rep. of Germany ...... 606/139

*Primary Examiner*—Stephen C. Pellegrino
*Assistant Examiner*—Jeffrey A. Schmidt
*Attorney, Agent, or Firm*—Townsend and Townsend Khourie and Crew

[57] ABSTRACT

The invention provides an apparatus and method for tissue ligation and transection. In a preferred embodiment, the apparatus comprises a shaft with a slot at the distal end in which a tissue structure may be positioned. A suture is mounted about the periphery of the slot with a free end of the suture on a first side of the slot and a knotted loop on a second side of the slot. The free end of the suture is retrieved and threaded through knotted loop so as to form a ligature surrounding the tissue structure. The free end is drawn proximally to tighten the ligature, and the knotted loops are cinched tight to lock the ligature in position. A blade slidably mounted in the shaft may be advanced to transect the tissue structure adjacent or between ligatures. A sleeve for compressing tissue within the slot during ligation, as well as electrodes for cauterizing the tissue, are also disclosed.

61 Claims, 12 Drawing Sheets

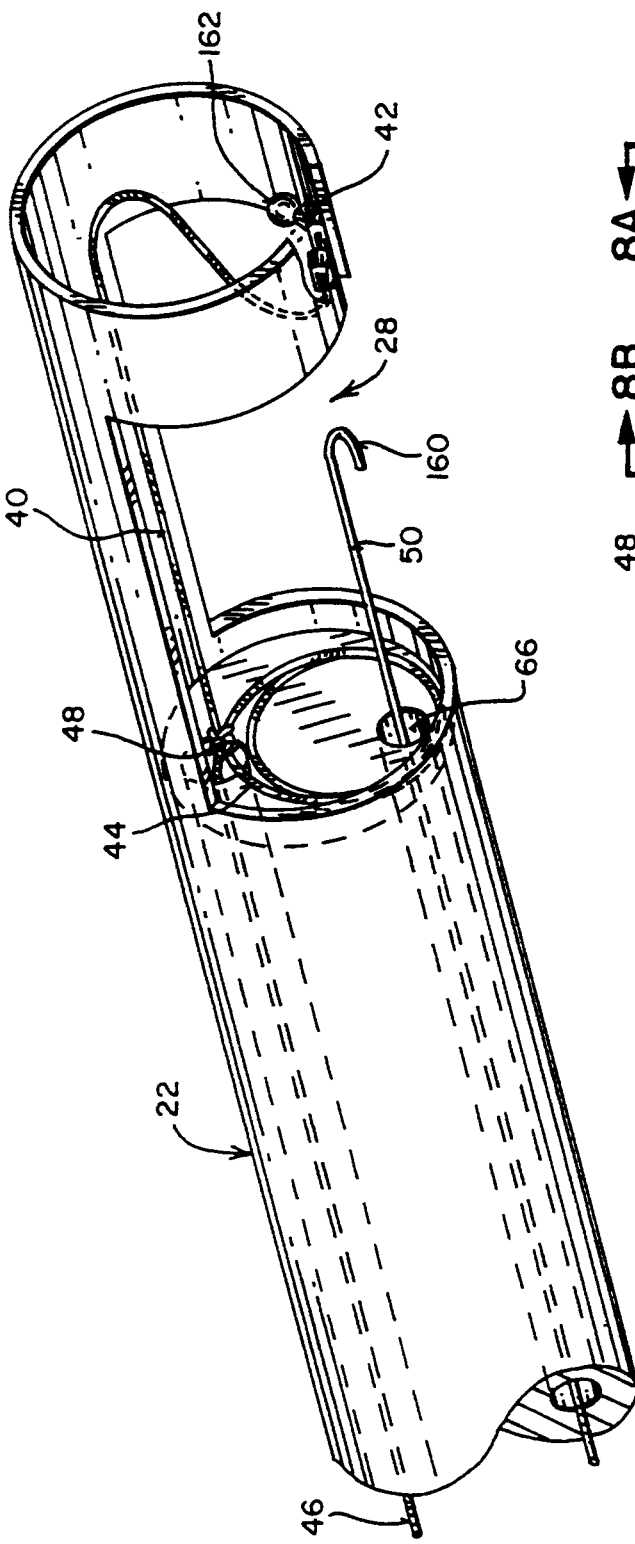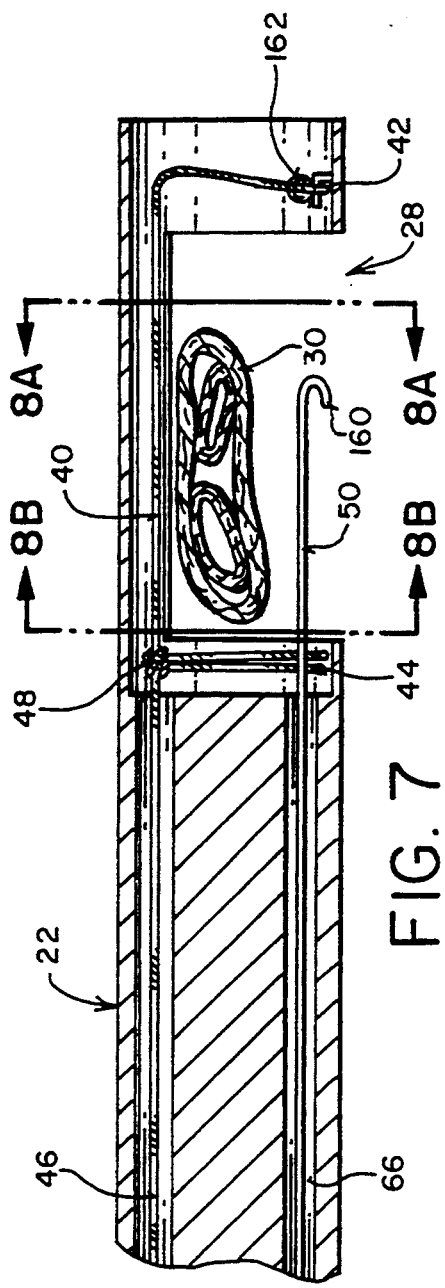
FIG. 6
FIG. 7

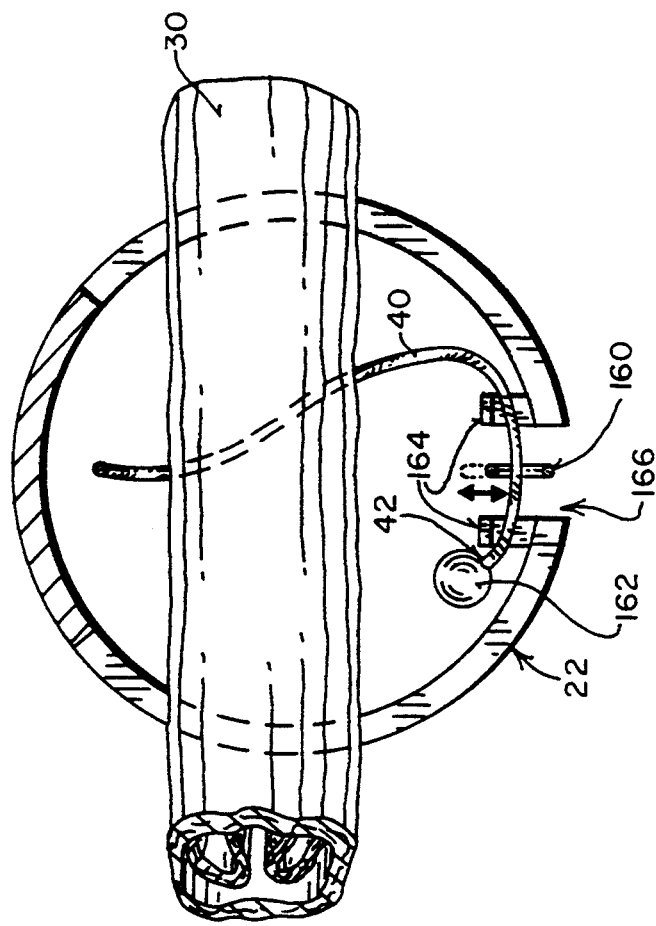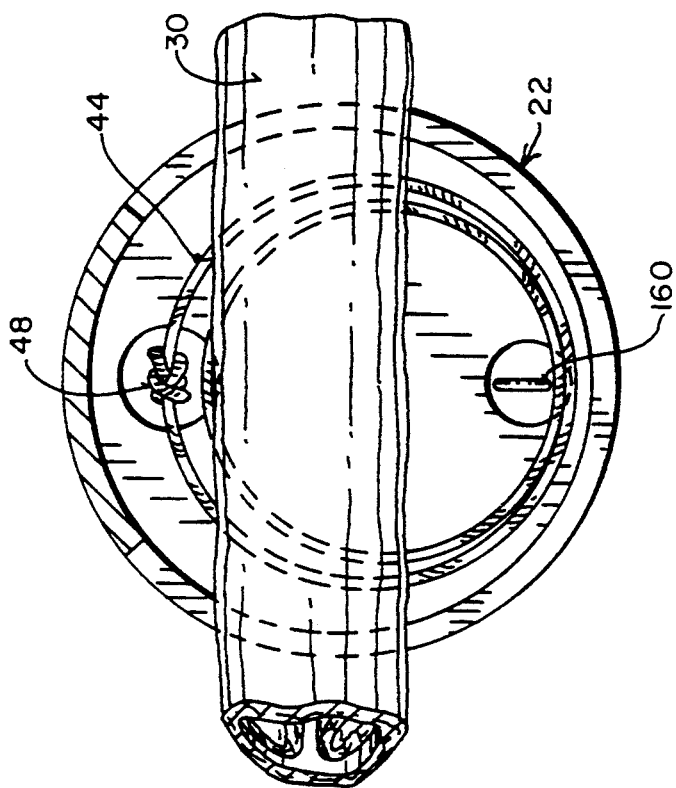

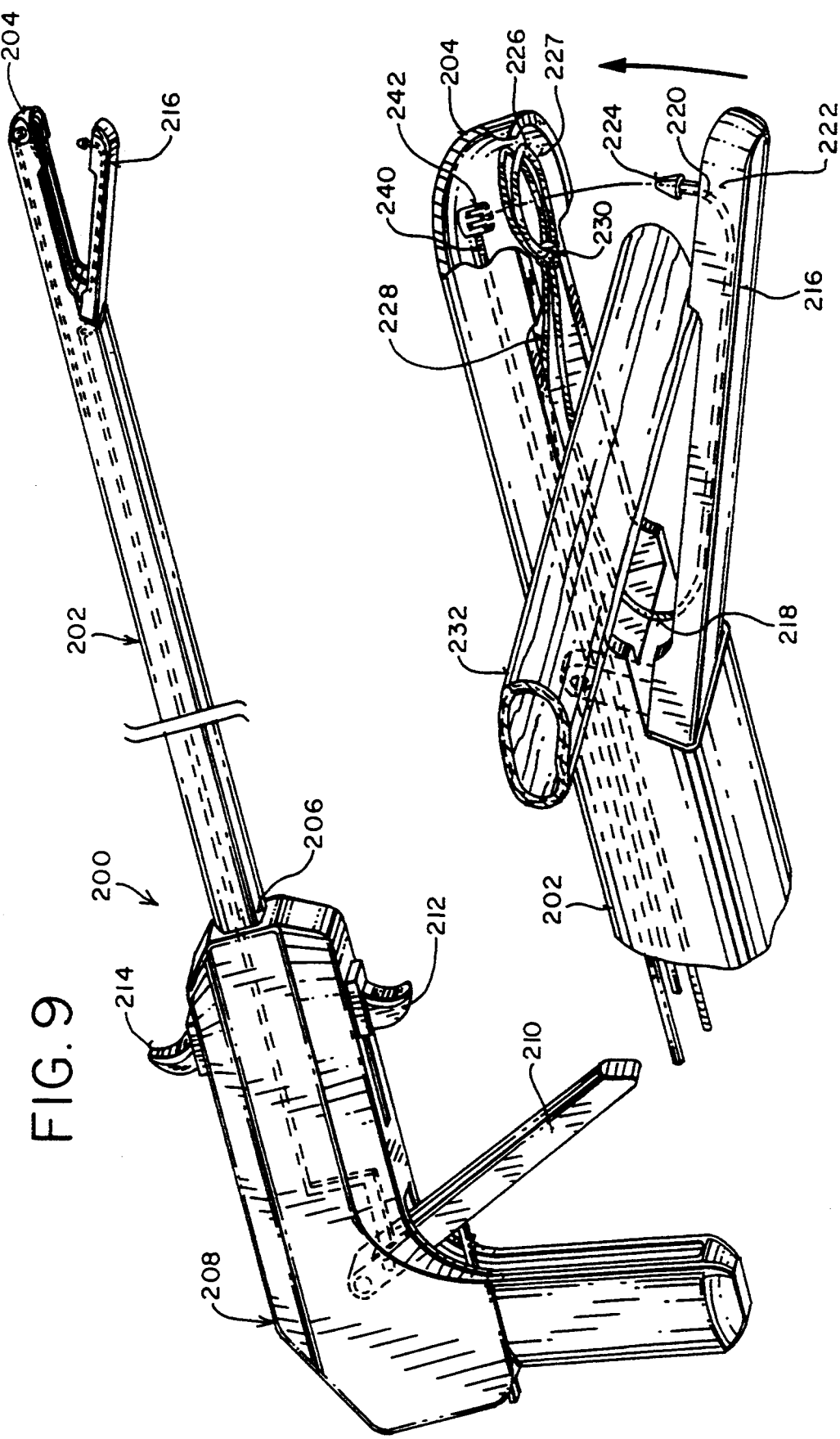

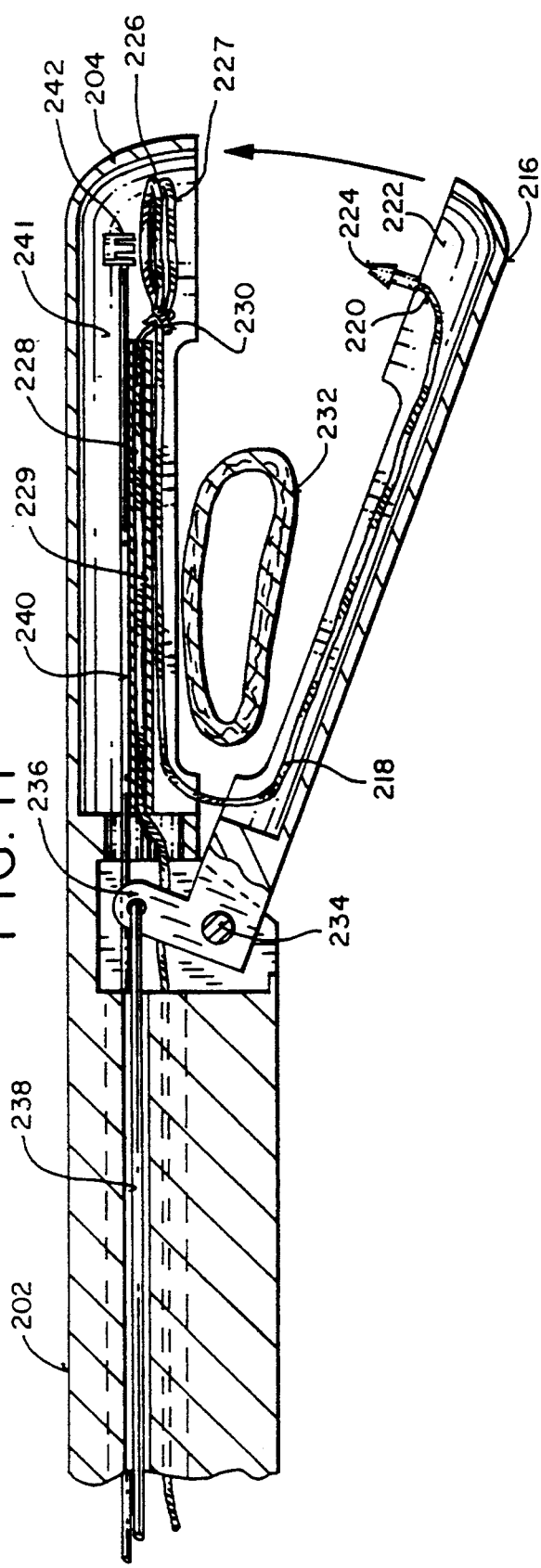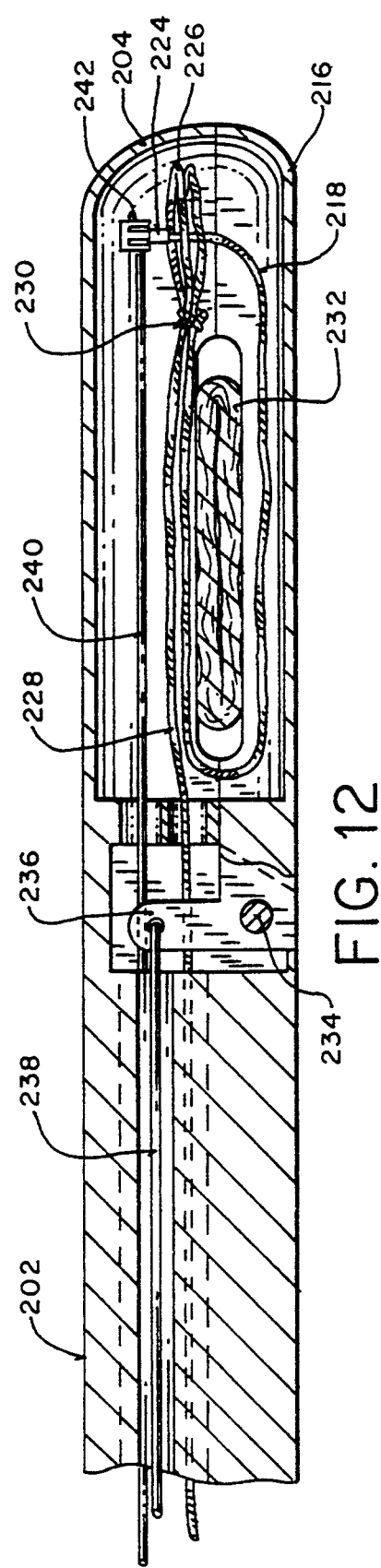

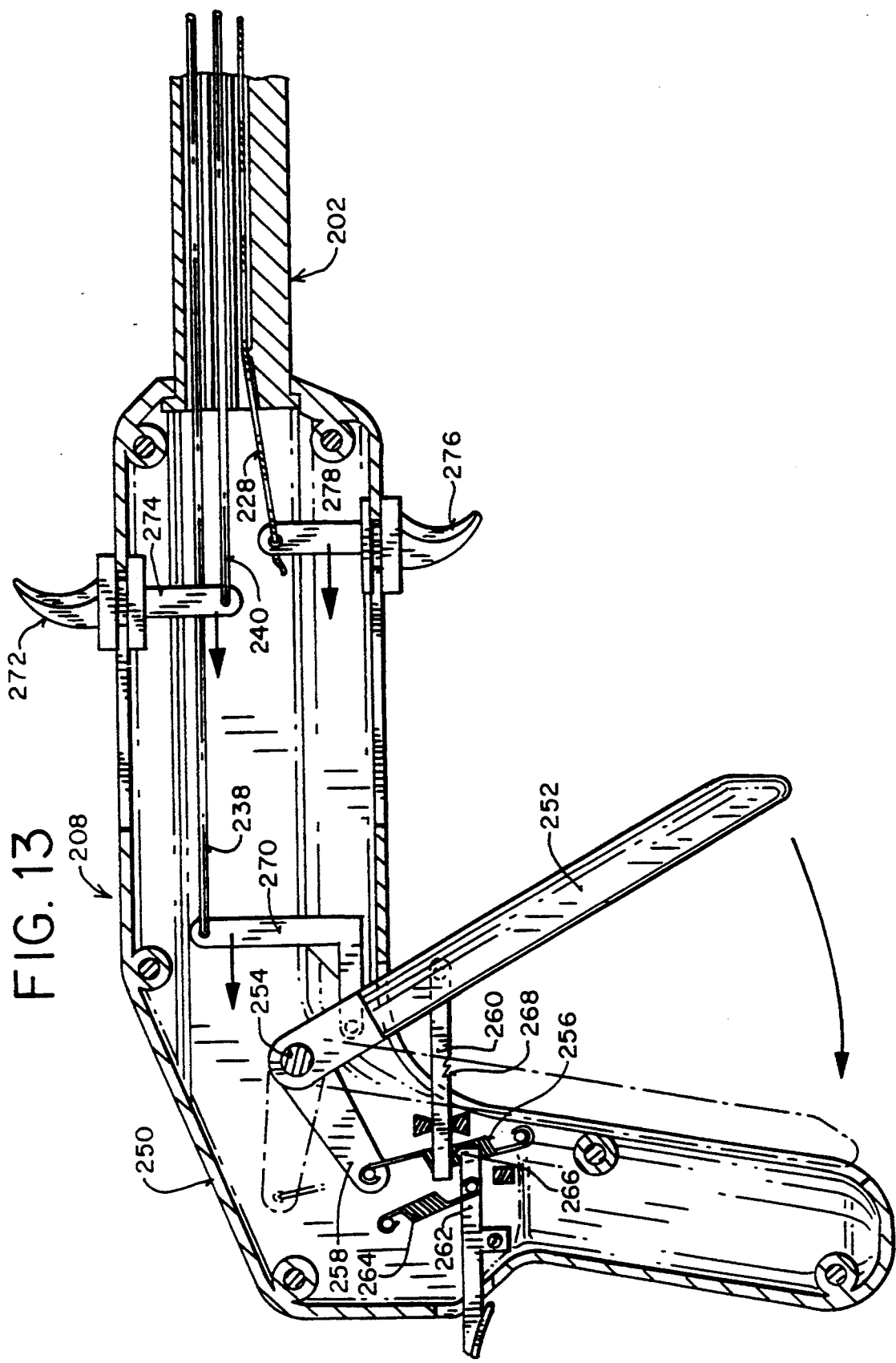

DUAL LIGATING AND DIVIDING APPARATUS

BACKGROUND OF THE INVENTION

The present invention relates generally to surgical instruments, and more specifically to endoscopic instruments for tissue ligation and transection.

In least invasive surgical procedures such as laparoscopy, endoscopy, pelviscopy and thoracoscopy, surgery may be performed within a body cavity without the need to make large incisions to provide access to the body cavity. In laparoscopy, for example, the abdomen is insufflated using a gas such as carbon dioxide. Surgery may then be performed within the abdominal cavity through access ports called trocar sleeves positioned through the abdominal wall. Such trocar sleeves provide a sealed entryway into the abdominal cavity through which long handled instruments may be introduced. To minimize trauma, the trocar sleeves are made of small cross-section, requiring surgical instruments which are also of very small cross-section, typically in the range of 3 to 15 mm in diameter. Such instruments must be elongated so as to reach a surgical site within the abdomen while having substantial rigidity for manipulation from the proximal end of the instrument. Further, laparoscopic instruments must be configured to seal within the trocar sleeve so as to prevent leakage of insufflation gas from the body cavity.

During many surgical procedures, including laparoscopic and other least invasive procedures, it is often necessary to ligate certain tissue structures. Such structures may include arteries, veins, biliary ducts, lymph ducts, uterine ligaments and other vessels and organs. Such structures are frequently continuous, or have no end proximate to the site to be ligated (in contrast to an appendage), and thus preclude the use of closed loop or noose-type ligatures.

Two techniques are currently used for ligating such continuous structures. In one technique, a U-shaped wire clip is positioned with the legs of the clips surrounding the structure, and the legs of the clip are closed tightly onto the structure. Exemplary devices for applying such surgical clips for tissue ligation are described in U.S. Pat. No. 4,616,650, U.S. Pat. No. 5,084,057 and U.S. Pat. No. 4,509,518, which are incorporated herein by reference.

A second technique for ligating continuous structures involves tying a length of suture about the structure either by hand, or using a suture applying instrument such as that described in U.S. Pat. No. 5,129,912, the complete disclosure of which is incorporated herein by reference.

While surgical clip application and suture tying are effective for ligation in certain procedures, such techniques suffer from several drawbacks. Surgical clips are ineffective for ligating larger tissue structures, as the clip legs often have insufficient length and/or spacing to completely surround such structures. For laparoscopic procedures, the small diameter of the trocar sleeves through which instruments are introduced limits the size of the surgical clip appliers and surgical clips which can be used. Surgical clips further suffer from the tendency to slip off the tissue structure after application due to insufficient clamp force of the clip legs.

Suture tying, on the other hand, requires difficult suture manipulation within the restricted surgical workspace and a high level of skill in knot-tying to provide effective ligation. Moreover, the limited size of trocar sleeves as well as the limited visibility afforded the surgeon during laparoscopic procedures greatly complicates the task of tying sutures within the body cavity for purposes of ligation.

While ligation is sometimes performed without tissue transection, ligation is frequently performed for the purpose of sealing off a duct, vessel or other structure to prevent the outflow of blood or other fluid when the structure is transected. When a tissue structure is to be transected, it is often desirable to ligate the structure at two or more locations so as to permit transection between the ligatures.

Devices are known which accomplish both ligation as well as transection of a tissue structure using a single instrument. Such devices are described in U.S. Pat. No. 3,584,628, U.S. Pat. No. 3,545,444, U.S. Pat. No. 3,006,344, U.S. Pat. No. 3,175,556, U.S. Pat. No. 3,735,762, U.S. Pat. No. 4,086,926 and U.S. Pat. No. 3,665,924, the complete disclosures of which are incorporated herein by reference. Generally, such devices apply a surgical clip or, in the case of the devices described in U.S. Pat. No. 3,545,444 or U.S. Pat. No. 3,584,628, a length of wire suture, to each of two locations on the tissue structure separated by a gap. The devices may further include a transecting blade slidable between the ligatures to transect the tissue.

While such ligation/transection devices offer greater convenience than techniques which require separate instruments for ligating and transecting a tissue structure, these devices continue to suffer from the drawbacks of conventional ligating instruments. That is, the clips or wire wraps applied by such devices are of insufficient size for ligating certain tissue structures. Devices suitable for laparoscopic use are particularly limited in size. Moreover, these clips or wraps suffer from the tendency to slip off of the tissue structure after application.

Improved apparatus and methods for ligating and transecting tissue structures are therefore desired which overcome the deficiencies of known devices. The apparatus and method should facilitate ligation at one, two or more sites on a tissue structure. In addition, the apparatus and method should permit ligation and/or transection of tissue structures of various sizes, including the larger vessels and ducts which cannot be ligated using known devices. Desirably, the apparatus and method will facilitate application of a ligature using surgical sutures, without requiring intricate suture manipulation or knot-tying skills. The apparatus and method will preferably allow application of at least two ligatures to a continuous tissue structure, as well as transection of the structure adjacent to or between the ligatures. Moreover, the apparatus and method should be useful in laparoscopic and other least invasive procedures as well as in open surgical procedures.

SUMMARY OF THE INVENTION

The invention provides apparatus and methods for ligation and/or transection of tissue in various surgical procedures, with particular usefulness in laparoscopic surgical procedures. The apparatus and method facilitate the application of one or more ligatures of flexible suture to a tissue structure in a manner which greatly simplifies the positioning of such a suture about the structure and eliminates the need for knot-tying skills. Ligatures may be applied to tissue structures of a variety of shapes and sizes, and will be particularly useful for ligation of continuous vessels and ducts. The apparatus and method further provide for transection of the tissue structure adjacent to one or more ligatures applied to the structure. In specific embodiments, the apparatus and method provide compression of the tissue structure to improve ligation, and may further facilitate cauterization of tissue before, during or after transection.

In a first embodiment, a ligating apparatus constructed in accordance with the present invention will comprise a shaft having a distal end, a proximal end and a slot near the distal end in which tissue may be positioned. A first suture will be detachably mounted at the distal end of the shaft, the suture having a free end disposed on a first side of the slot, a knotted loop disposed on a second side of the slot opposite the free end, and a cinching line extending proximally from the knotted loop. The apparatus will further include means for threading the free end through the knotted loop while tissue is positioned in the slot such that the suture forms a ligature surrounding the tissue. The means for threading the free end through the knotted loop may be a variety of structures, including a slidable rod extending through the knotted loop for retrieving the free end and drawing it through the knotted loop. Alternatively, the means for threading the free end through the knotted loop may comprise a movable jaw pivotally coupled to the shaft near the distal end, the jaw forming one side of the slot. The free end of the suture will be disposed on a distal end of the jaw such that by closing the jaw, the free end will be threaded through the knotted loop.

The apparatus of the invention further includes means for tightening the ligature by pulling the free end relative to the knotted loop. This will usually comprise a slidable rod disposed in the shaft which draws the free end proximally so as to close the ligature about the tissue structure.

Additionally, the device will include means for cinching the knotted loop so as to lock the ligature. This will ordinarily be accomplished by pulling proximally on the cinching line by means of an actuator at the proximal end of the shaft.

The means for tightening the ligature by pulling proximally on the free end of the suture will utilize means at its distal end for retrieving the free end. The means for retrieving may take several forms, including a snap fitting which engages a snap attached to the free end of the suture. Alternatively, the means for retrieving may comprise a hook at the end of the slidable rod which engages anchor means at the free end of the suture. The anchor means may comprise a ball fixed at the free end, or a knot tied in the free end.

The apparatus of the invention may further provide means for cauterizing tissue disposed in the slot at the distal end of the shaft. In one embodiment, this will comprise at least one electrode disposed adjacent the slot which contacts tissue in the slot to cauterize the tissue. In addition, the apparatus may include means for compressing tissue within the slot to facilitate ligation, cauterization and/or transection of the tissue. The compression means will preferably comprise a sleeve slidably disposed about the shaft which can be translated distally to compress tissue against the distal side of the slot. The sleeve may have electrodes along its distal surface for cauterization purposes.

The apparatus may further include means for dividing tissue in the slot. In a particular embodiment, the means for dividing will comprise a cutting blade slidably disposed in the shaft adjacent to the first suture. The blade may be translated in the distal direction using an actuator at the proximal end of the shaft so as to transect the tissue lying in the slot.

Usually, the apparatus of the invention will facilitate application of two or more ligatures to the tissue structure simultaneously. In one embodiment, two sutures are disposed on the shaft generally parallel to one another, with a cutting blade slidably disposed between the sutures. In this way, the sutures may be positioned around the tissue structure to form a pair of ligatures, the ligatures tightened and locked, and the blade actuated so as to transect the tissue between the ligatures. In alternative embodiments, two or more ligatures may be disposed on each side of the cutting blade, or the ligatures may be applied only on one side of the cutting blade.

In an exemplary embodiment, the apparatus will further comprise means in the shaft for trimming off the free ends and/or cinchlines of the sutures after the ligatures have been tightened and locked. The trimming means will preferably comprise one or more trim blades slidably mounted in the shaft to be movable in the transverse direction. The trim blades will preferably be coupled to a pin which rides within an angled slot in the tissue-cutting blade. As the cutting blade moves distally to transect tissue, the pin and trim blades attached thereto are guided transversely across the shaft. The trim blades are configured to engage and sever the free end and cinchlines of the sutures, thereby disengaging the ligatures from the apparatus.

In the method of the present invention, a tissue structure may be ligated using an apparatus having a shaft with a distal end and a proximal end, whereby the apparatus is positioned such that a portion of the body structure is within a slot at the distal end of the shaft, with a free end of a first suture being disposed on one side of the slot and a knotted loop in the suture being disposed on an opposing side of the slot. The free end of the suture is then threaded through the knotted loop such that the suture forms a first ligature surrounding the structure. The free end of the suture is then retrieved with the distal end of a rod slidably disposed in the shaft and the ligature is tightened around the structure by sliding the rod in a proximal direction. The ligature is then locked by cinching the knotted loop, usually by means of an actuator coupled to the proximal end of the apparatus, the actuator being connected to a cinchline extending proximally from the knotted loop.

In a preferred embodiment of the method of the invention, a second suture is disposed at the distal end of the shaft generally parallel to the first suture, the second suture having a second free end and a second knotted loop on opposing sides of the slot. The method will further comprise the steps of threading the second free end through the second knotted loop such that the second suture forms a second ligature surrounding the structure. The second free end will be retrieved with a distal end of a second rod slidably disposed in the shaft. The second suture will then be tightened around the structure by sliding the second rod in a proximal direction and the second knotted loop will be cinched closed using the actuator, again coupled to a second cinchline extending from the second knotted loop to the actuator.

In an exemplary embodiment, the method will also comprise a step of dividing the body structure between the first and second sutures after the steps of tightening the first and second knotted loops.

The step of threading the free end through the knotted loop may be accomplished in a variety of ways, including extending a rod having a snap fitting at its distal end to engage a snap at the free end of the suture, or closing a movable jaw at the distal end of the apparatus, the free end of the suture being disposed on the jaw so as to be threaded through the knotted loop as the jaw is closed.

The method may further include the steps of cauterizing tissue by means of electrodes mounted adjacent the slot, as well as compressing tissue in the slot during ligation, cauterization and/or division the tissue.

A further understanding of the nature and advantages of the invention may be realized by reference to the remaining portions of the specification and the drawings.

BRIEF DESCRIPTION OF THE DRAWINGS

FIG. 6 is a perspective view of a distal portion of the apparatus of FIG. 1, showing an alternative embodiment of the means for retrieving the free end of the suture.

FIG. 7 is a front cross-sectional view of the distal portion of the apparatus of FIG. 6.

FIGS. 8A and 8B are transverse cross-sectional views through the slot at the distal end of the shaft in FIG. 6.

FIG. 9 is a perspective view of an alternative embodiment of a ligating and dividing apparatus constructed in accordance with the principles of the present invention.

FIG. 10 is a perspective view of a distal portion of the apparatus of FIG. 9, showing a tissue structure positioned in the movable jaw.

FIG. 11 is a front cross-sectional view of the distal portion of the apparatus of FIG. 10, showing the jaw in an open position.

FIG. 12 is a front cross-sectional view of the distal portion of the apparatus of FIG. 10, showing the jaw in a closed position.

FIG. 13 is a front cross-sectional view of the handle of the apparatus of FIG. 9.

DESCRIPTION OF SPECIFIC EMBODIMENTS

Figure 1:
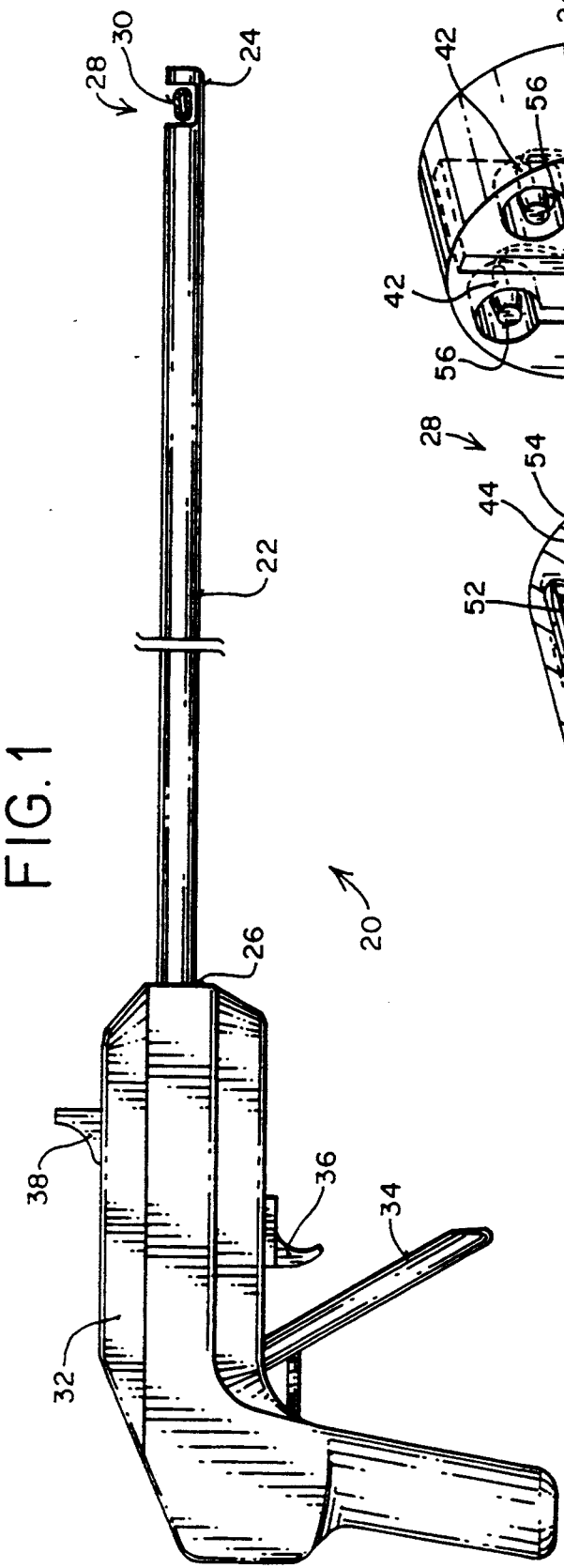
FIG. 1 is a front elevational view of a ligating and dividing apparatus constructed in accordance with the principles of the present invention.

The apparatus of the present invention will be described with reference to FIGS. 1–14. In a first specific embodiment, illustrated in FIG. 1, ligating and dividing apparatus 20 comprises an elongate shaft 22 having a distal end 24 and a proximal end 26. A slot 28 is disposed near distal end 24 of shaft 22, slot 28 being open on a lateral side. A tissue structure 30 is shown positioned within slot 28. Shaft 22 is attached at its proximal end 26 to a handle 32 suitable for gripping using a single hand. In a preferred embodiment, shaft 22 will be mounted to handle 32 such that shaft 22 is rotatable about its longitudinal axis, allowing slot 28 to be positioned at a variety of radial orientations. Coupled to handle 32 are several actuators 34, 36, 38, which will be described below.

While the apparatus of the invention will be useful in a variety of surgical procedures, in a preferred embodiment, ligating and dividing apparatus 20 will be configured for use in laparoscopic and other least invasive surgical procedures. The ligating and dividing apparatus 20 will preferably be configured for sealable introduction through a trocar sleeve or similar cannula of small cross-section. Preferably, shaft 22 will be less than 12 mm in diameter, with a length in the range of 20 to 30 cm. Shaft 22 will further be internally sealed by means of gaskets and/or sealants to prevent leakage of insufflation gas through the shaft. Shaft 22 may be a variety of materials, including rigid plastic or biocompatible metal such as stainless steel.

In an exemplary embodiment, handle 32 will be reusable and sterilizable between uses, while all or a portion of shaft 22 will be disposable. In one embodiment, a distal portion of shaft 22 will comprise a removable cartridge (described below) which includes slot 28 and the ligature material to be applied to tissue structure 30. Alternatively, all of shaft 22 will be disposable, and proximal end 26 will be removably attached to handle 32 by conventional means.

Figure 2:
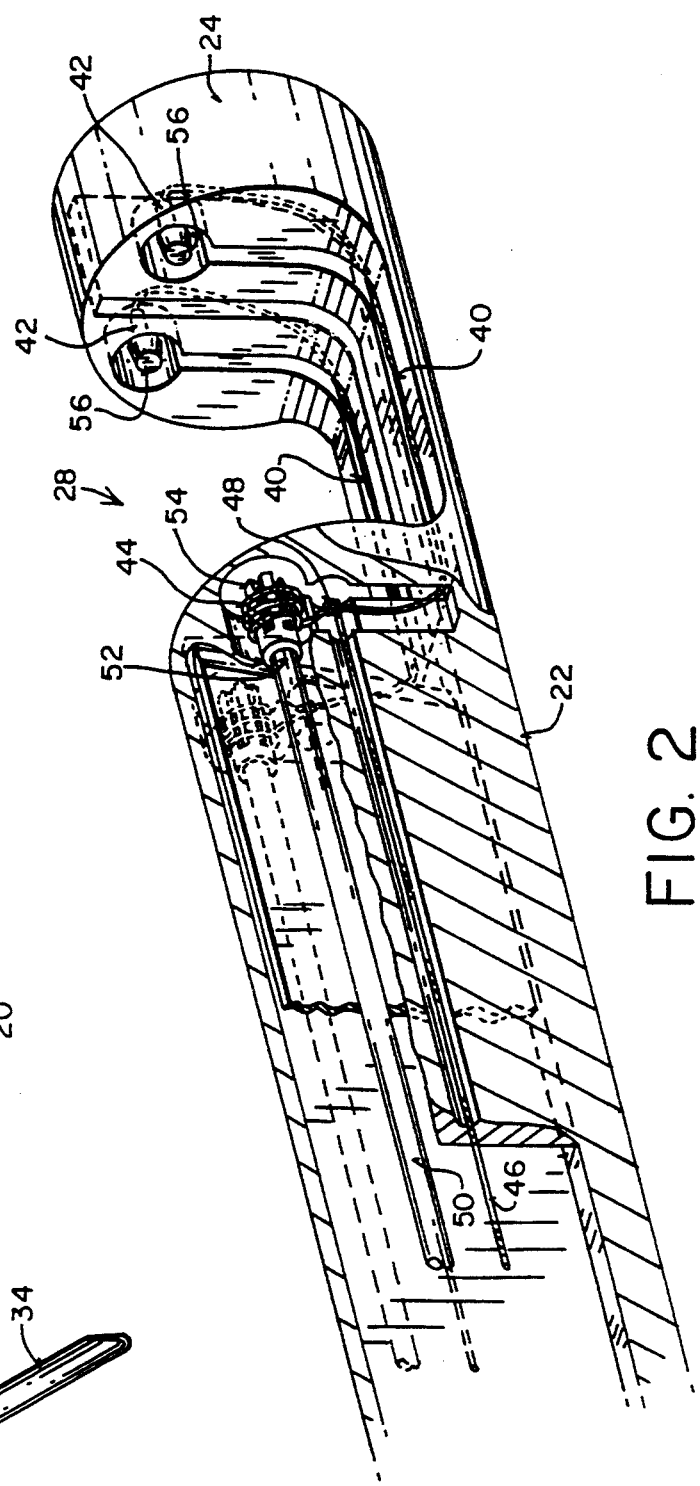
FIG. 2 is a cutaway perspective view of a distal portion of the apparatus of FIG. 1.

Referring now to FIG. 2, a distal portion of shaft 22 will be more fully described. Slot 28 forms a receiving space in which a tissue structure may be positioned for ligation and/or transection. Of particular advantage in the apparatus of the present invention is the ability to make slot 28 of any desired length, facilitating ligation of tissue structures which are significantly larger than those which can be ligated using conventional instruments.

A pair of sutures 40 are disposed in the shaft so as to surround three sides of slot 28. Sutures 40 have free ends 42 mounted at the distal side of slot 28, and knotted loops 44 mounted at a proximal side of slot 28. Cinchlines 46 extends proximally from knots 48 forming knotted loops 44. Usually, knots 48 will comprise slip knots, whereby exerting tension on cinchlines 46 will cause knotted loops 44 to close.

In a first preferred embodiment, knotted loops 44 are disposed about capture rods 50 slidably disposed in shaft 22. At the distal ends 52 of capture rods 50, snap fittings 54 are attached. Snap fittings 54 are configured to engage with snaps 56 attached to the free ends 42 of sutures 40. By sliding capture rods 50 distally within knotted loops 44, snaps 56 become engaged in snap fittings 54. By then sliding capture rods 50 proximally, free ends 42 may be drawn through knotted loops 44, forming a ligature around the tissue structure.

Figure 3A:
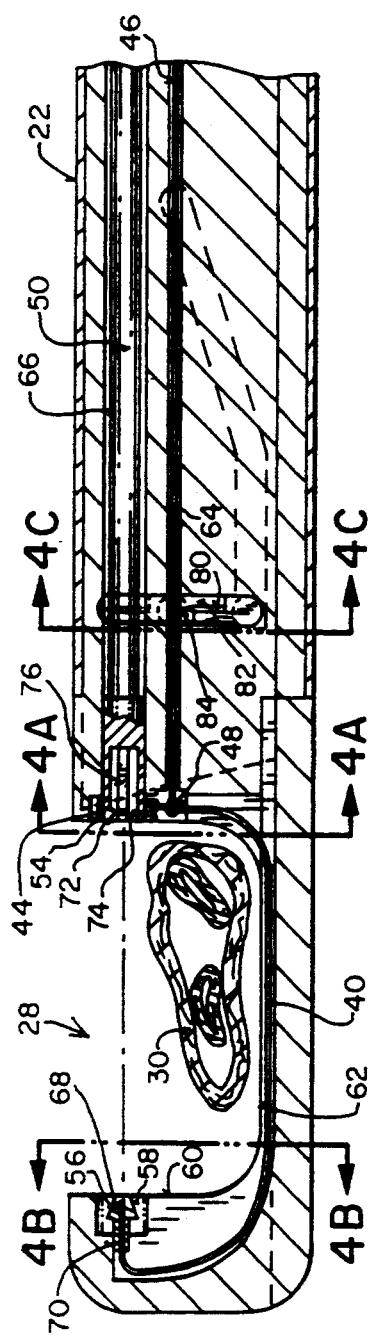
FIG. 3A is a front cross-sectional view of the distal portion of the device of FIG. 1 showing the sutures and capture tubes of the device.

Referring now to FIG. 3A, snaps 56 are disposed in a recess 58 along the proximally-facing surface 60 of slot 28. Sutures 40 are disposed in a channel 62 in shaft 22 about the periphery of slot 28. Snap fittings 54 and knotted loops 44 are disposed in a recess 57 in the distally-facing surface 61 of slot 28. Cinchlines 46 extend proximally from knotted loops 48 through axial passages 64 in shaft 22. Capture rods 50 are slidably disposed within passages 66 in shaft 22.

Figure 4C:
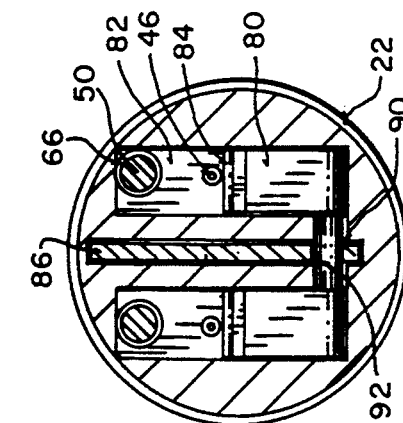
FIGS. 4A–4C are transverse cross-sectional views at various positions in the distal portion of the shaft of the device of FIG. 1.
Figure 4B:
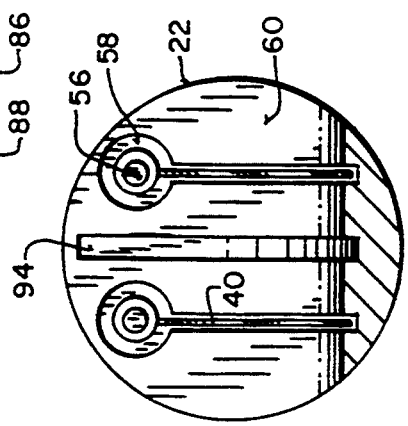
Figure 4A:
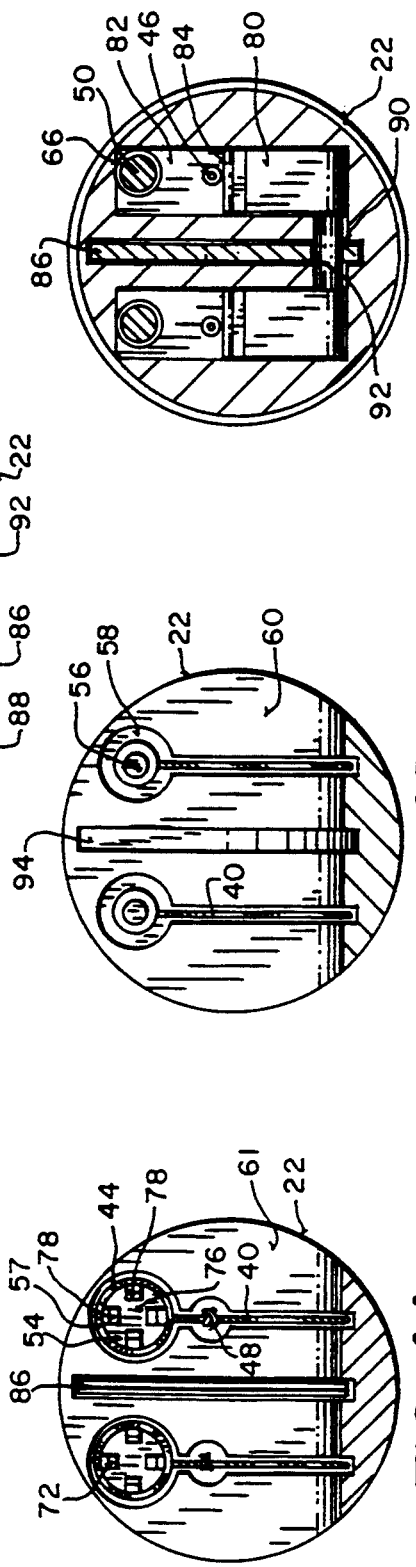

Snaps 56 comprise a tapered head 68 connected to a reduced diameter neck 70. Snap fitting 54 has a complementary configuration, with a tapered inlet 72 forming a collar 74 about a central aperture 76. As best seen in FIG. 4A, snap fitting 54 will usually be divided into a plurality of prongs 78 configured to flex resiliently outward as snap fitting 54 is inserted over snap 56. It may be seen that tapered inlet 72 will slide along tapered head 68 of snap 56 to its proximal edge, wherein the resilient prongs 78 will snap inwardly against neck 70 so as to retain snap 56 within aperture 76.

Referring again to FIG. 3A, a pair of trim blades 80 are disposed within a transverse passage 82 in shaft 22. A sharpened edge 84 of each blade 80 is disposed to pass through passages 64, 66 as the blade slides in a transverse direction, as illustrated in FIG. 4C. This facilitates severing the free end and the cinchline of suture 40 from the ligature after it has been tightened and locked.

Figure 3B:
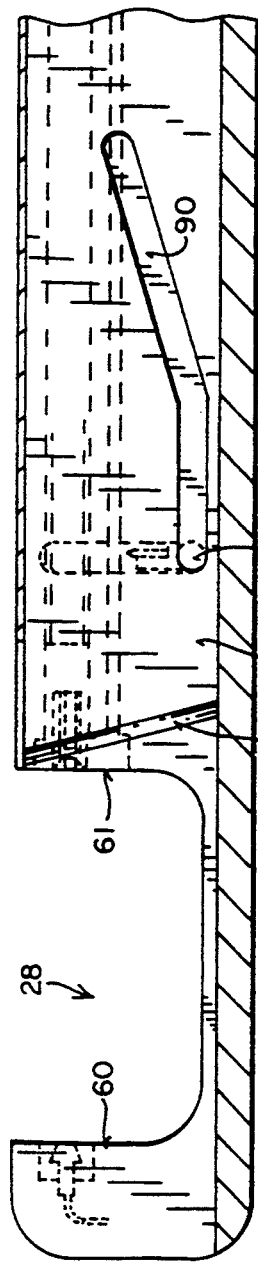
FIG. 3B is a front cross-sectional view of the distal portion of FIG. 2, showing the cutting blade of the apparatus.

Referring now to FIG. 3B, a blade 86 is slidably disposed in shaft 22 between capture rods 50 (shown also in FIG. 4A). Blade 86 has a sharpened distal edge 88. Blade 86 may slide distally through slot 28 to transect tissue lying therein. Referring to FIG. 4B, proximally-facing surface 60 of slot 28 includes an aperture 94 for receiving distal edge 88 of blade 86. Blade 86 also includes an angular slot 90 which serves to actuate trim blades 80 as blade 86 moves in a distal direction. As seen in FIG. 4C, trim blades 80 are connected to a shaft 92 which extends through angular slot 90 in blade 86. By translating blade 86 in a distal direction, shaft 92 rides within angular slot 90 and is pushed in a transverse direction, causing trim blades 80 to pass through passages 64, 66 through which free ends 42 and cinchlines 46 extend.

Figures 5A, 5B:
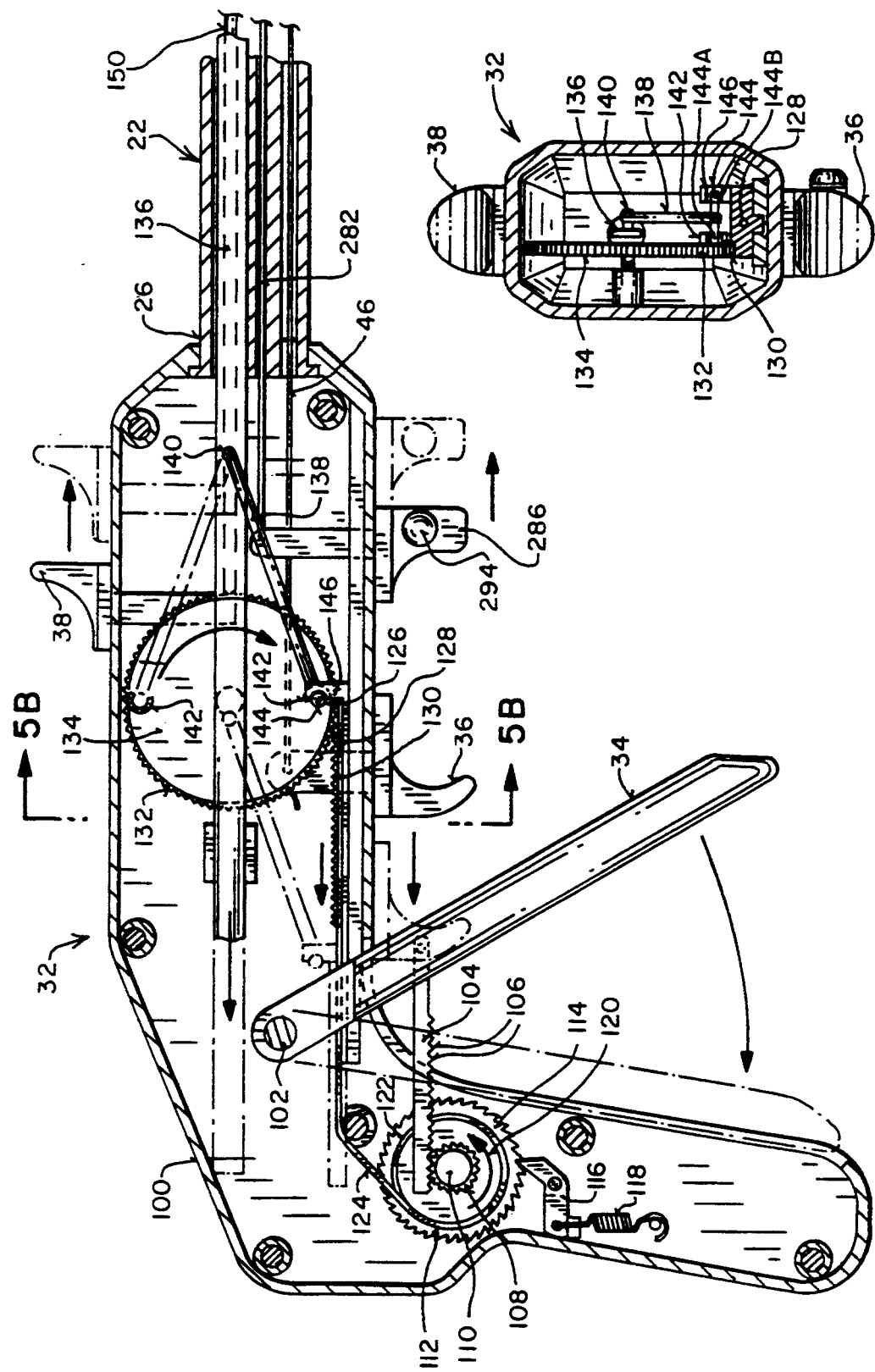
FIG. 5A is a front cross-sectional view of the handle and actuator mechanism of the apparatus of FIG. 1.
FIG. 5B is a transverse cross-section view through the handle of FIG. 5A.

Referring now to FIGS. 5A–5B, handle 32 of the ligating apparatus will be more fully described. Handle 32 includes a housing 100, which may be plastic, metal or a variety of other rigid materials. Capture tube actuator 34 is coupled to housing 100 at pivot point 102. A rack member 104 is pivotally coupled to actuator 34 and extends proximally into housing 100. Rack member 104 has gear teeth 106 which mesh with gear teeth 108 on an inner pinion 110. A ratchet wheel 112 is attached to pinion 110 so as to rotate therewith. Ratchet teeth 114 on ratchet wheel 112 are engaged by a pall 116 coupled to housing 100 and biased against ratchet wheel 112 by a spring 118. Pinion 110 and ratchet wheel 112 will therefore rotate only in the direction of arrow 120.

Ratchet wheel 112 has a track 122 about which is wound a flex cable 124. Flex cable 124 is attached at its opposing end 126 to a sled 128 which slides in an axial direction within housing 100. Sled 128 has a plurality of teeth 130 which engage gear teeth 132 about the periphery of a pinion 134 rotatably coupled to housing 100.

A linkage 136 extends through shaft 22 and is coupled at its distal end to capture rods 50 (not shown in FIG. 5). Linkage 136 is mounted so as to be slidable in the axial direction within housing 100 and shaft 22. A connecting rod 138 is pivotally coupled to linkage 136 by a pivot 140. At its opposing end, connecting rod 138 has a transverse pin 144. Pin 144 will extend outward on both sides of connecting rod 188, with one end 144a supported in a support cup 142 on pinion 134 and the opposing end 144b extending away from pinion 134. Support cup 142 will have a diameter slightly larger than pin 144 and will be slightly more than semi-circular to provide a snap fit of pin 144 therein. Sled 128 has a hook 146 at its distal end configured to engage end 144b of pin 144 in the position shown in FIG. 5B.

When lever 34 is pivoted in a proximal direction, rack member 104 turns pinion 110, winding flex cable 124 onto track 122. Flex cable 124 pulls sled 128 proximally, causing pinion 134 to rotate. Connecting rod 138 is initially in an upper position as shown in phantom in the figure, with pin 144 supported in cup 142. As pinion 134 rotates, connecting rod 138 pushes linkage 136 first in a distal direction, causing capture rods 50 to extend distally to engage snaps 56 at the free ends of sutures 40 (see FIG. 2). Further rotation of pinion 134 pulls connecting rod 138 and linkage 136 in a proximal direction, causing capture rods 50 to slide proximally, pulling free ends 42 of the sutures through knotted loops 44. When pinion 134 rotates to the position shown in FIG. 5A, pin 144 is at its lowermost position where it is engaged by hook 146 on sled 128. Sled 128 moves further proximally, pulling pin 144 and connecting rod 138 with it. Capture rods 50 thereby move proximally to tighten the ligature about the tissue structure.

When the ligature has been pulled to the desired tightness about the tissue structure, knotted loops 44 may be cinched to lock the ligature. This is accomplished by cinch actuator 36 slidably coupled to housing 100. Cinchlines 46 extending through shaft 22 from knotted loops 44 are attached to cinch actuator 36 within housing 100. When the ligature has been tightened, cinch actuator 36 may be pulled proximally to cinch knotted loops 44 closed, thereby locking the ligature about the tissue structure.

Where the tissue structure is to be transected between the tightened ligatures, blade actuator 38 is utilized. Blade actuator 38 is slidably coupled to housing 100. A blade extension 150 extends proximally from blade 86 and is connected to blade actuator 38. By sliding blade actuator 38 in a distal direction, blade 86 moves distally across slot 28, severing the tissue structure therein. At the same time, as described above, trim blades 80 are actuated so as to severe cinchlines 46 and free ends 42 attached to capture rods 50.

Figure 16:
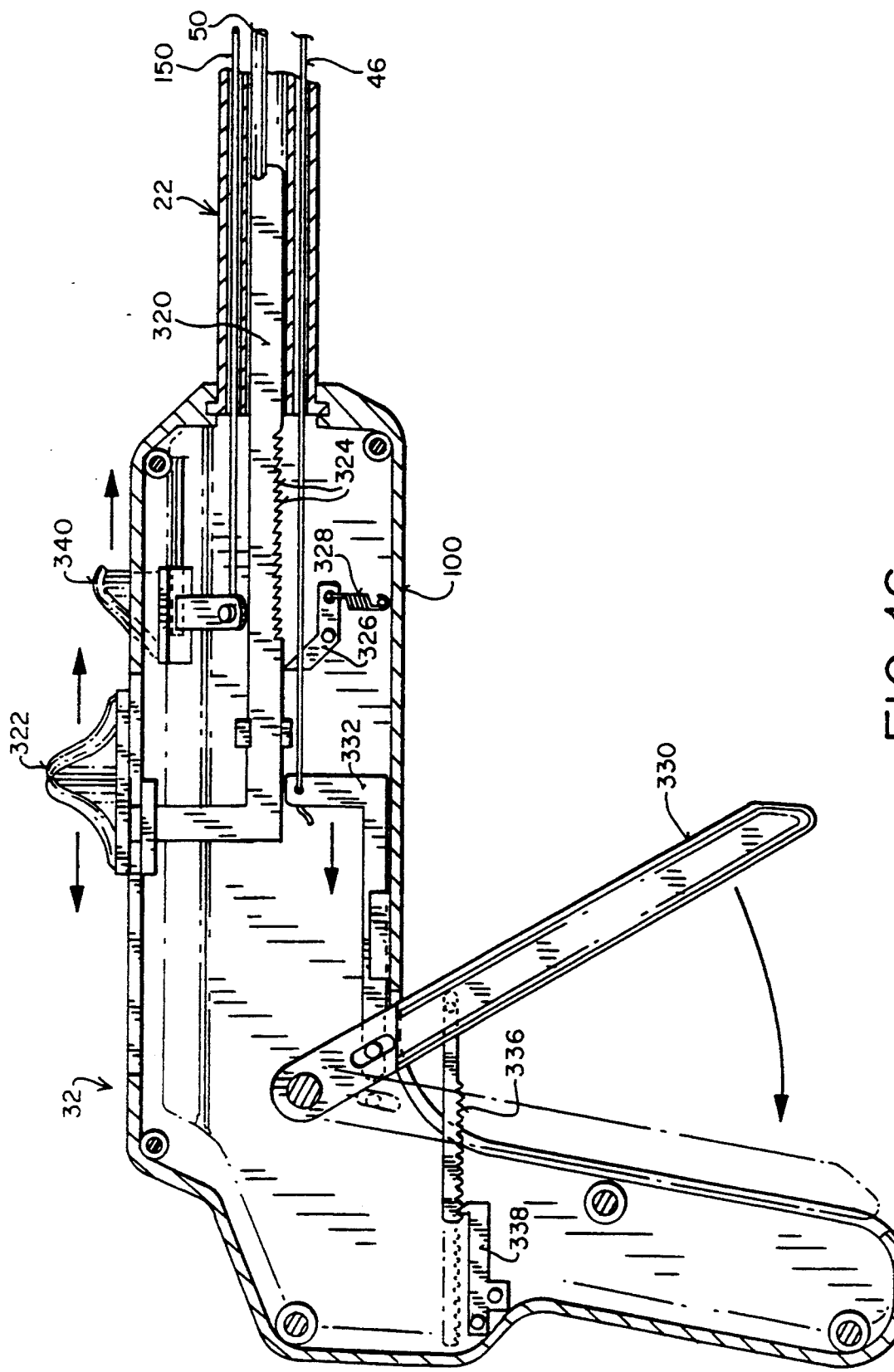
FIG. 16 is a front cross-sectional view of an alternative embodiment of the handle of the apparatus of FIG. 1.
Figure 17:
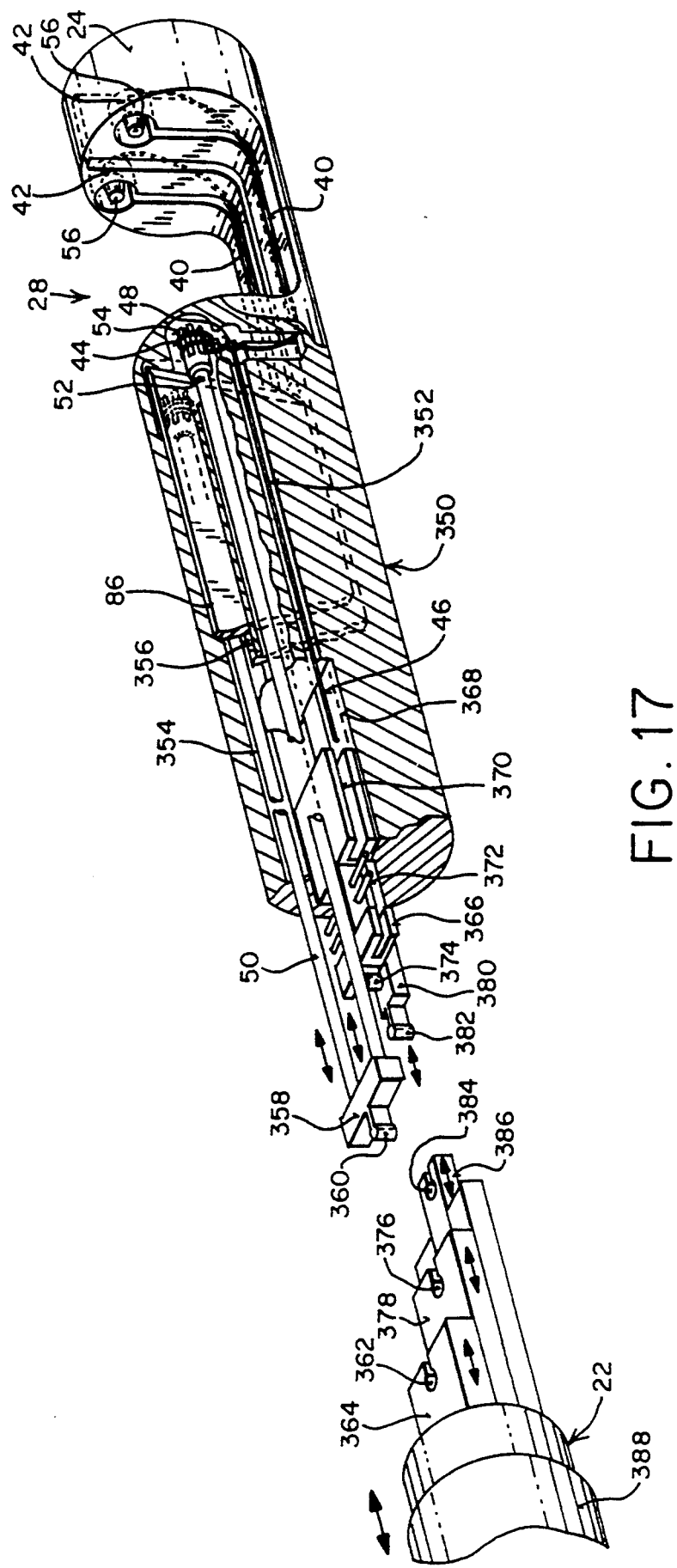
FIG. 17 is a perspective cut-away view of a disposable cartridge for removable attachment to the shaft of an apparatus constructed in accordance with the principles of the present invention.

An alternative embodiment of handle 32 is illustrated in FIG. 16. In this embodiment, capture rods 50 are coupled at their proximal ends to a linkage 320 within housing 100. A capture rod actuator 322 is slidably mounted to housing 100 and coupled to linkage 320. A plurality of ratchet teeth 324 are disposed along a lower surface of linkage 320 and are engaged by a pawl 326 biased against the linkage by a spring 328. Actuator 322 may slide distally to extend capture rods 50 across slot 28 so as to engage snaps 56 in snap fittings 54. Actuator 322 may then slide proximally to pull free ends 42 through knotted loops 44. At a predetermined position, linkage 320 will have been retracted far enough that pawl 326 engages teeth 324, allowing the ligature to be tightened about the tissue structure and maintained in position without continuing to hold actuator 322.

To lock the ligature after tightening, lever 330 is pulled proximally, pulling an extension 332 to which is coupled cinchline 46. A ratchet arm 334 connected to lever 330 has a plurality of teeth 336 engaged by a pawl 338, providing ratcheted cinching of knotted loops 44.

Once the ligatures have been tightened and locked, the tissue structure may be transected using blade actuator 340 slidably mounted to housing 100. Distal movement of actuator 340 pushes blade extension 150 distally, transecting the tissue structure with blade 86.

In an exemplary embodiment, illustrated in FIG. 1.7, a detachable, disposable cartridge 350 will be provided for attachment to a distal end of shaft 22. Cartridge 350 will have a structure similar to the distal portion of shaft 22 illustrated in FIGS. 2–4 above, and will contain sutures 40 disposed about the periphery of slot 28, snaps 56 at the free ends of the sutures, knotted loops 54 and cinchlines 46 extending through passages 352. Capture rods 50 will be slidably disposed within passages 354 with snap fittings 54 mounted at their distal ends. Blade 86 will be slidable within a central channel 356 and across slot 28 for tissue transection.

Capture rods 50 will be connected at their proximal ends to a block 358, which has an interconnect 360 extending proximally therefrom. Interconnect 360 is received in aperture 362 at a distal end of linkage 364, slidably disposed within shaft 22. Linkage 364 will be coupled at its proximal end (not shown) to the capture rod actuator or handle 32 (see FIGS. 5 and 16).

Cinchlines 46 are connected at their proximal ends to a slidable block 366 disposed in a slot 368 within cartridge 350. Preferably, block 366 will include a channel 370 along each of its side surfaces through which cinchlines 46 will extend. A pair of transverse pins 372 are mounted to block 366 to which cinchlines 46 may be tied. An interconnect 374 extends from the proximal end of block 366 and is received in an aperture 376 a the distal end of linkage 378. Linkage 378 is slidably disposed in shaft 22 adjacent capture rod linkage 364, and is coupled at its proximal end to a cinchline actuator on handle 32 (FIGS. 5, 16).

A blade extension 380 is attached at its distal end to blade 86 and is slidably disposed in a passage in cartridge 350. At its proximal end, blade extension 380 has an interconnect 382 configured to be received in an aperture 384 at distal end of blade linkage 386. Blade linkage 386 is coupled at its proximal end to a blade actuator on handle 32 (FIGS. 5, 16).

Advantageously, cartridge 350 may be easily attached to shaft 22 simply by sliding interconnects 360, 374, 382 into apertures 362, 376, 384 the distal ends of linkages 364, 378, 386. A sleeve 388 is slidably disposed about shaft 22, which is then slide distally over cartridge 350 up to the proximal side of slot 28, thereby stabilizing and aligning cartridge 350 with shaft 22. The device is then operable in the manner described in connection with the embodiment illustrated in FIGS. 1–5. Following ligation and transection, cartridge 350 may be detached by retracting sleeve 388 and disconnecting interconnects 360, 374, 382. The cartridge may then be discarded and additional cartridges loaded for use in the same or future procedures. After a procedure is completed, the handle and shaft portions of the device may be sterilized for further use.

A second preferred embodiment of the ligating apparatus of the present invention is illustrated in FIGS. 6–8. For purposes of illustration, the embodiment of FIGS. 6–8 is shown with a single suture and without a cutting blade for dividing tissue. However, it should be understood that, as with the device of FIGS. 1–5, the ligating apparatus of FIGS. 6–8 may have two or more sutures for applying multiple ligatures to a tissue structure. Further, the device may include a cutting blade for dividing tissue between or adjacent the ligatures applied.

Referring to FIGS. 6 and 7, suture 40 surrounds slot 28 with a free end 42 detachably mounted on the distal side of slot 28. Knotted loop 44 is mounted proximal to slot 28, and cinchline 46 extends proximally from knot 48. Capture rod 50 extends through a passage 66 in shaft 22 through knotted loops 44. In place of snap fittings 54 of FIGS. 1–4, capture rod 50 has a hook 160 at its distal end. Hook 160 may be extended across slot 28 to snare free end 42 of suture 40. To facilitate retaining free end 42 in hook 160, an anchor 162 is fixed to free end 142. Anchor 162 may comprise a ball of metal or plastic as shown in the figures, or alternatively, anchor 162 may comprise simply a knot in suture 40 near free end 42.

Referring to FIGS. 8A and 8B, free end 42 of suture 40 is retained in a pair of L-shaped brackets 164 which face in a proximal direction. Free end 42 extends across a slot 166 formed between brackets 164. When capture rod 50 is extended distally, a distal side of hook 160 contacts free end 42 where it crosses slot 166. This deflects hook 160 upward, as shown in FIG. 8B, such that the hook passes over free end 42. When hook 160 is distal to free end 42, capture rod 50 may be drawn proximally to pull free end 42 across slot 28, surrounding tissue structure 30 with a ligature formed by suture 40. Anchor 162 prevents free end 42 from slipping through hook 160. Free end 42 is drawn through knotted loops 44 and further proximally through passage 66 to tighten the ligature. Cinchline 46 is then pulled proximally to tighten knotted loop 44, locking the ligature in place.

The device of FIGS. 6–8 may further include a blade as shown in FIGS. 1–4, which could be actuated to divide tissue within slot 30. Usually, two or more sutures will be disposed in shaft 22 so that two or more ligatures are applied to the tissue structure. The blade will preferably be slidably mounted between the sutures so as to transect the tissue between ligatures.

Referring now to FIGS. 9–13, a further embodiment of the apparatus of the invention will be described. Ligating apparatus 200 will include a shaft 202 having a distal end 204 and a proximal end 206. Proximal end 206 will be fixed to a handle 208, to which are coupled a plurality of actuators 210, 212 and 214. A movable jaw 216 is coupled to shaft 202 near distal end 204. As in the above embodiments, shaft 202 will usually be configured for use in laparoscopic surgery, and will have shape and dimensions suitable for introduction through a trocar sleeve or other cannula into a body cavity.

Referring now to FIGS. 10–12, a suture 218 is mounted at the end of shaft 202 with a free end 220 mounted to a distal portion 222 of jaw 216. Free end 220 may be retained in distal portion 222 of jaw 216 by various means, such as a slot or channel in jaw 216 which is slightly narrower than the width of suture 218 so as to frictionally retain the suture. Preferably, a snap 224 will be fixed to free end 220 to facilitate retrieval as described below.

Knotted loops 226 are retained in an aperture 227 near the distal end of shaft 202 opposite the distal end of jaw 216. Preferably, two or more knotted loops are formed in the suture. A cinchline 228 extends proximally through passage 229 in shaft 202 from a slip-knot 230 forming knotted loops 226. As described above, exerting tension on cinchline 228 will close knotted loops 226. A capture rod 240 is slidably disposed in a passage 241 in shaft 202. Capture rod 240 has a snap fitting 242 at its distal end which is disposed opposite snap 224 on jaw 216.

A tissue structure 232 is positioned between Saw 216 and shaft 202. Jaw 216 is coupled to shaft 202 by a pin 234 and includes an arm 236 to which is coupled a linkage 238. By moving linkage 238 in the proximal direction, jaw 216 pivots toward shaft 202, clamping tissue structure 232 therebetween. As jaw 216 closes, snap 224 on free end 220 is threaded through knotted loops 226 and engages snap fitting 242, as shown in FIG. 12. Advantageously, the conical shape of snap 224 facilitates penetration of any tissue, e.g. mesentery tissue, which might be disposed between snap 224 and snap fitting 242 as jaw 216 is closed.

The ligature formed about tissue structure 232 is tightened by drawing capture rod 240 in the proximal direction. The free end of the suture is thereby drawn proximally, tightening the ligature about tissue structure 232. Cinchline 228 may then be pulled in the proximal direction to close knotted loops 226, locking the ligature.

In an alternative embodiment, the apparatus of FIGS. 9-13 may have a hook at the distal end of capture rod 240, with anchor means such as a ball on free end 220, much like those illustrated in FIGS. 6-8. In this embodiment, closure of jaw 216 will thread the anchor means through knotted loops 226 and position the anchor means for engagement by the hooked end of capture rod 240. Proximal movement of the capture rod will then tighten the ligature about tissue structure 232.

It should be understood that, as with the embodiments described above, the embodiment of FIGS. 9-13 may have two or more sutures mounted in the device for simultaneous application of multiple ligatures to the tissue structure. Moreover, the device may include a blade for transecting tissue structure 232 after the ligatures have been applied. Trim blades for severing cinchline 228 and free end 220 may further be included as in previous embodiments.

Referring now to FIG. 13, the handle of the embodiment of FIG. 9 will be described. Handle 208 comprises a housing 250 of metal, plastic or other rigid material. A jaw actuator 252 is pivotally coupled to housing 250 by pin 254. A spring 256 exerts tension on an arm 258 attached to actuator 252 to bias the actuator in an outward position. An extension 260 extends from actuator 252 into housing 250 and is engaged by a pall 262 biased against extension 260 by a spring 264. Pall 262 has a tooth 266 for engaging notches 268 in extension 260.

Coupling 270 pinned to actuator 252 is coupled to linkage 238, which is connected to movable jaw 216 at the distal end of shaft 202. By pulling actuator 252 in a proximal direction, linkage 238 is drawn proximally so as to close jaw 216.

A tightening actuator 272 is slidably mounted to housing 250 and has an extension 274 to which capture rod 240 is attached. Actuator 272 may be moved in the proximal direction to pull capture rod 240 and the free end of suture 218 proximally, tightening the ligature about the tissue structure.

A cinch actuator 276 is slidably mounted to housing 250 and includes an extension 278 to which cinchline 228 may be attached. When the ligature has been drawn to the desired degree of tightness about the tissue structure, actuator 276 may be pulled in the proximal direction to close knotted loops 226, locking the ligature.

The apparatus may further include a blade for dividing the tissue structure, which would be linked to an additional actuator on handle 208 in a manner similar to that described above in connection with FIGS. 1-5. The apparatus may further be designed for applying multiple ligatures, in which case a plurality of capture rods would be coupled to actuator 272, and a plurality of cinchlines would be attached to actuator 276.

Figure 14:
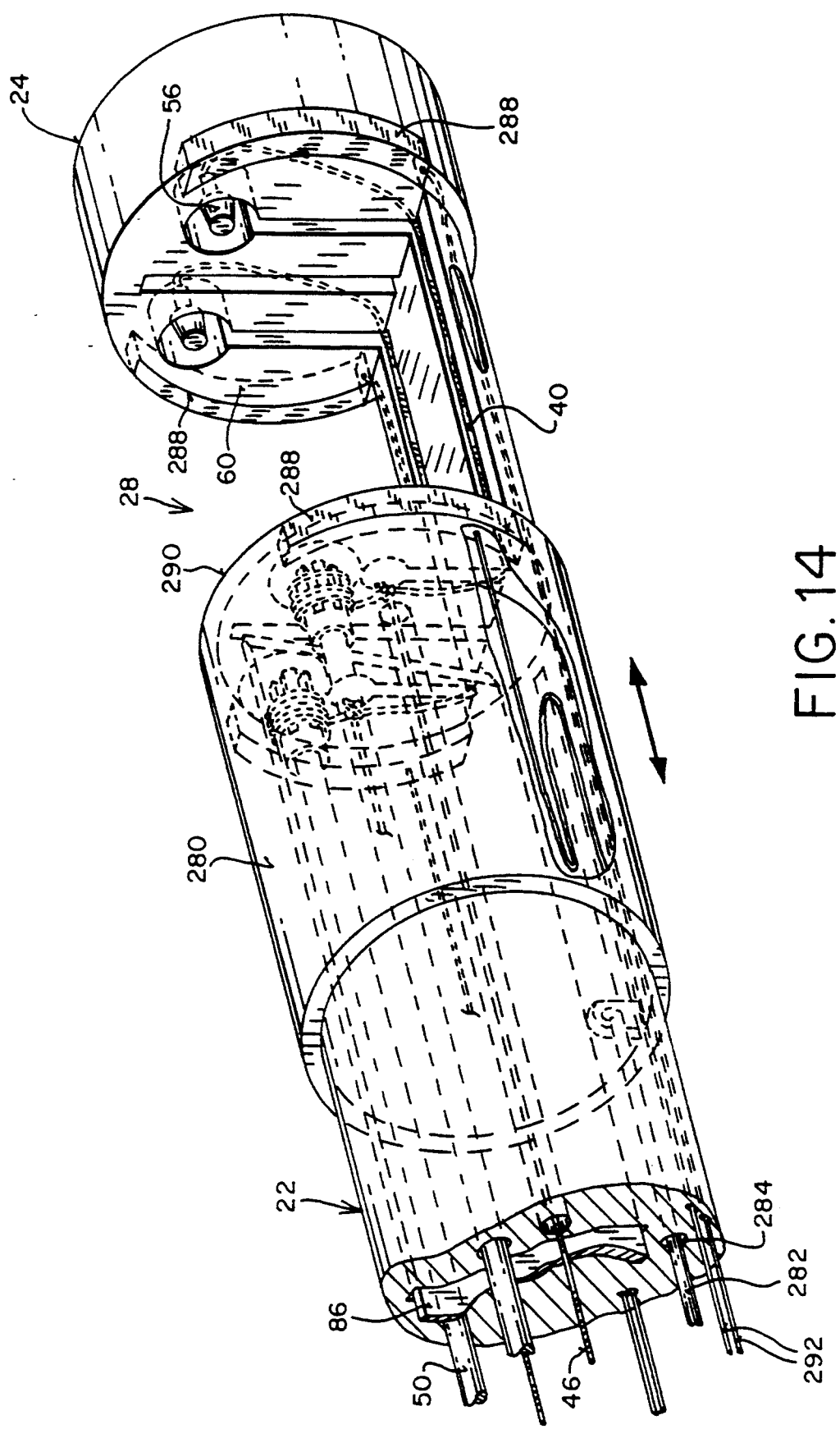
FIG. 14 is a perspective partial cutaway view of a distal portion of the apparatus of FIG. 1, showing the slidable sleeve for compressing tissue and electrodes for cauterization.

In a further embodiment of the apparatus of invention, illustrated in FIG. 14, means are provided for compressing tissue within slot 28 during ligation and/or transection of the tissue structure. The means for compressing tissue will be described in connection with the embodiment of FIGS. 1-5, but it will be understood that the compressing means will have equal applicability to other embodiments of the invention described above.

In a first embodiment, the means for compressing tissue will comprise a sleeve 280 slidably mounted to shaft 22 proximal to slot 28. Sleeve 280 will be attached to a linkage 282 extending through a passage 284 in shaft 22. As shown in FIG. 5, linkage 282 will be coupled to an actuator 286 slidably mounted to handle 32. By pushing actuator 286 distally, sleeve 280 is translated across slot 28, compressing the tissue structure against proximally-facing surface 60.

In a further embodiment, the apparatus will comprise means for cauterizing tissue within slot 28. The cauterizing means, in an exemplary embodiment, will comprise a plurality of electrodes 288 disposed on opposing sides of slot 28. In one embodiment, electrodes 288 will be mounted adjacent surface 60 of slot 28, and along the distal end 290 of sleeve 280. Electrodes 288 will be supplied with current through electrode wires 292 extending through shaft 22 to handle 32, where the wires are coupled to a switch 294 on sleeve actuator 286 (see FIG. 5A). Switch 294 will be connected to an external power supply (not shown). Sleeve 280 may be slid distally to compress the tissue within the slot, and switch 294 may be actuated to supply current to electrodes 288, thereby cauterizing tissue in the slot. Ligatures may then be applied, tightened and locked about the tissue structure. Blade 86 may then be actuated to transect the tissue.

Referring now to FIGS. 15A-15E, the method of the invention will be described. While the method will be described with reference to the embodiment of FIGS. 1-5, it will be understood that the method of the invention may be performed using the apparatus of any of the embodiments described above.

Figure 15A:
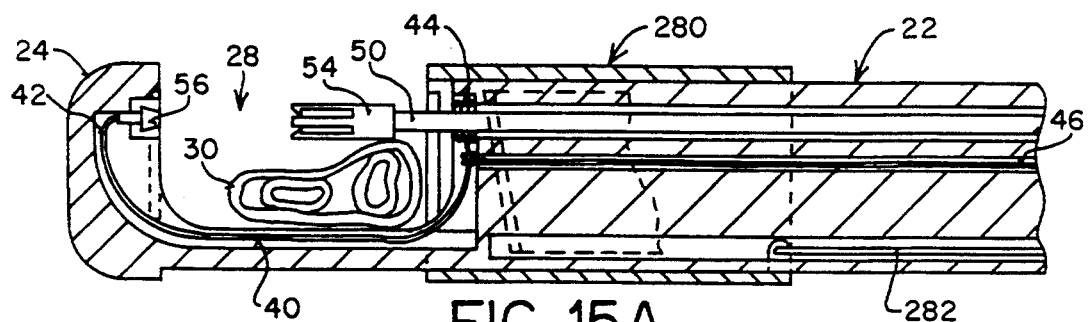
FIGS. 15A–15E are front cross-sectional view of a distal portion of the apparatus of FIG. 1, illustrating the method of the present invention.
Figure 15B:
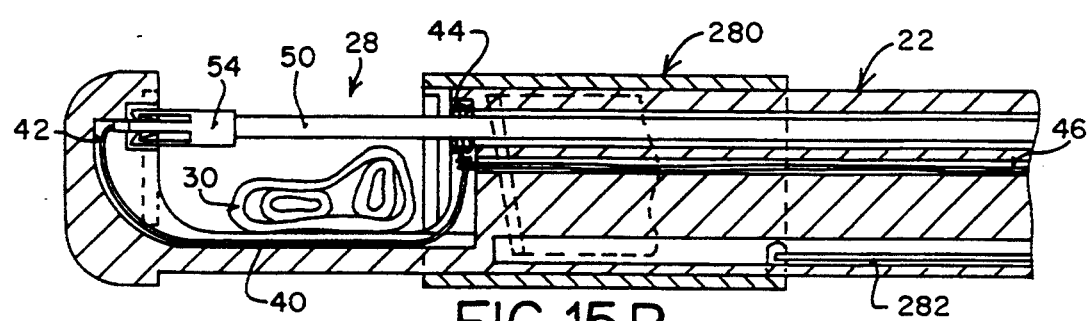

In a preferred embodiment, the method comprises positioning the tissue structure 30 within slot 28 at the distal end of shaft 22. The tissue structure may comprise, for example, an artery, vein, biliary duct, lymph duct or uterine ligament. With the tissue structure positioned in slot 28, capture rods 50 are extended distally using actuator 34 on handle 32. As illustrated in FIG. 15B, capture rods 50 are extended until snap fittings 54 engage snaps 56 attached to the free ends 42 of sutures 40.

Figure 15C:
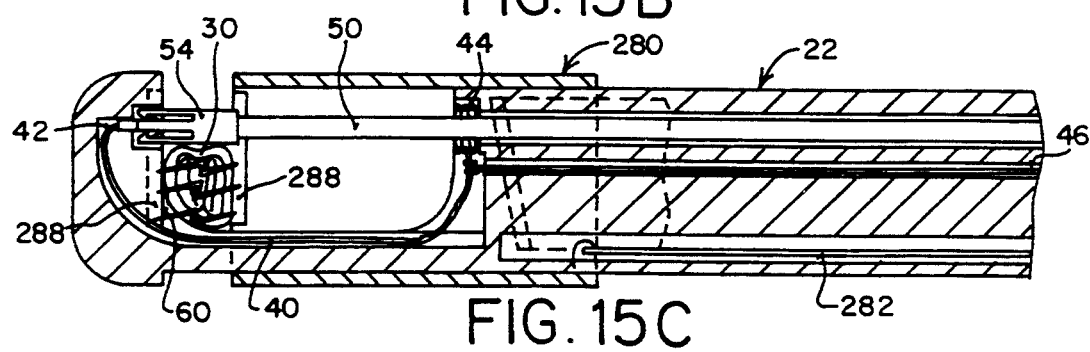

In an exemplary embodiment, tissue 30 may be compressed within slot 28 as shown in FIG. 15C. With snap fittings 54 engaged with snaps 50, sleeve 280 is moved distally so as to compress tissue structure 30 against distal surface 60 of slot 28. In a further embodiment, current may be supplied to electrodes 288 to cauterize tissue structure 30.

Figure 15D:
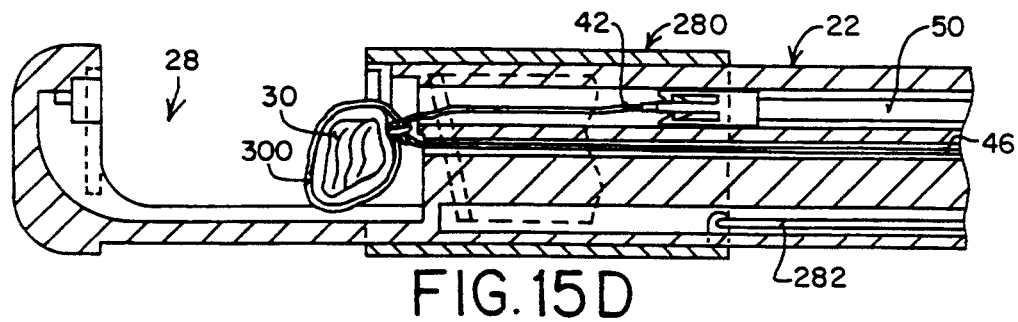
Figure 15E:
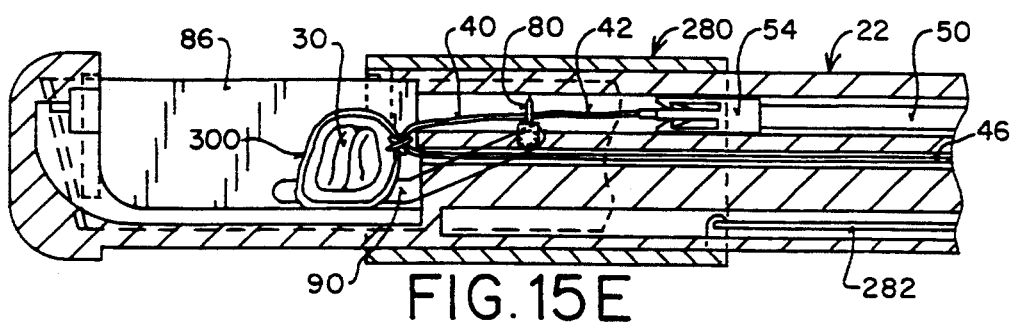

Following cauterization, capture rods 50 are drawn in a proximal direction, threading free ends 42 of the sutures through knotted loops 44. Free ends 42 are drawn proximally by capture rods 50 until the ligatures 300 formed about tissue structure 30 are tightened, as shown in FIG. 15D. Cinchlines 46 are then pulled proximally to close knotted loops 44, locking ligatures 300 about the tissue structure.

When ligatures 300 have been tightened about tissue structure 30, blade 86 may be actuated to transect the tissue structure between ligatures 300. At the same time, trim blades 80 will be actuated so as to sever free ends 42 and cinchlines 46 of sutures 40.

It should be understood that, according to the principles of the present invention, the method may include applying one or a plurality of ligatures to the tissue structure. The tissue structure may or may not be transected after the ligatures are applied, and transection may occur between ligatures or adjacent one or more ligatures. The method may or may not be performed with steps of tissue compression and cauterization. Moreover, the method may include positioning the tissue structure between movable jaw 216 and the distal end of the shaft of the apparatus illustrated in FIGS. 9–12. As described above, the jaw is closed on the tissue to thread the free end of the suture through the knotted loop, as well as to compress the tissue between the jaw and the distal portion of the shaft. Cauterization could be accomplished in the moveable jaw embodiment by electrodes mounted to the jaw and/or the distal end of the shaft.

The method will be particularly useful in laparoscopic procedures, wherein the apparatus will be introduced through a trocar sleeve or similar cannula into a body cavity. Usually, the body cavity will be insufflated using an insufflation fluid such as gaseous $CO_2$. Visualization will be facilitated by means of a laparoscope inserted into the body cavity and connected to an external video monitor. In order to maintain insufflation of the body cavity, the shaft of the ligating apparatus will be configured to seal within the trocar sleeve.

The present invention thus provides an apparatus and method for ligating and transecting a continuous tissue structure such as an artery, vein, duct or ligament which overcomes many of the drawbacks of known devices. In particular, the apparatus and method facilitate ligation of tissue structures of various size including those substantially larger than can be ligated using conventional surgical clips. Moreover, the apparatus and method allow the application of flexible sutures to a tissue structure, forming a ligature which resists slippage and conforms to various and amorphous shapes. Further, such sutures can be applied without the need for intricate manipulation of the suture or knot-tying skills. Further, the apparatus and method facilitate ligation, transection, compression and cauterization using a single device which may be held in a single hand of the user, thus simplifying and accelerating tissue ligation and transection procedures.

While the above is a complete description of the preferred embodiments of the invention, various alternatives, modifications and equivalents may be used. Therefore, the above description should not be taken as limiting the scope of the invention which is defined by the appended claims.

What is claimed is:

1. Ligating apparatus comprising:
   a shaft having a distal end, a proximal end, and a slot near the distal end in which tissue may be positioned;
   a first suture detachably mounted at the distal end, the suture having a free end disposed on a first side of the slot, a knotted loop disposed on a second side of the slot opposite the free end and a cinching line extending proximally from the knotted loop;
   means attached to the shaft for threading the free end through the knotted loop while tissue is positioned in the slot such that the suture forms a ligature surrounding the tissue;
   means attached to the shaft for tightening the ligature by pulling the free end axially relative to the shaft; and
   means attached to the shaft for cinching the knotted loop by pulling proximally on the cinching line.

2. The apparatus of claim 1 wherein the threading means comprises a rod slidably mounted to the shaft and extending through the knotted loop with means at a distal end thereof for retrieving the free end of the suture.

3. The apparatus of claim 2 wherein the suture further comprises anchor means at the free end for engaging the retrieving means.

4. The apparatus of claim 3 wherein the anchor means comprises a snap fixed to the free end, the retrieving means comprising a snap fitting for engaging the snap.

5. The apparatus of claim 3 wherein the retrieving means comprises a hook for engaging the anchor means.

6. The apparatus of claim 5 wherein the anchor means comprises a ball fixed to the free end.

7. The apparatus of claim 5 wherein the anchor means comprises a knot tied in the free end.

8. The apparatus of claim 2 wherein the rod is slidable proximally along the shaft with the free end attached thereto to tighten the ligature.

9. The apparatus of claim 1 further comprising a movable jaw pivotally coupled to the shaft near the distal end, the jaw forming one side of the slot.

10. The apparatus of claim 9 wherein the jaw has a proximal end coupled to the shaft and a distal end on which the free end of the suture is disposed, the knotted loop being disposed on the shaft opposite the free end, whereby closure of the jaw toward the shaft threads the free end through the knotted loop.

11. The apparatus of claim 10 wherein the suture further comprises anchor means attached to the free end.

12. The apparatus of claim 11 wherein the means for retrieving comprises a hook for engaging the anchor means.

13. The apparatus of claim 11 wherein the anchor means comprises a ball fixed to the free end.

14. The apparatus of claim 1 further comprising a second suture detachably secured to the shaft generally parallel to the first suture and spaced apart therefrom.

15. The apparatus of claim 14 further comprising a cutting blade slidably disposed in the shaft adjacent the first suture for dividing tissue.

16. The apparatus of claim 1 further comprising means at the proximal end of the shaft for sequentially actuating the threading means, tightening means and cinching means.

17. The apparatus of claim 1 further comprising a trimming blade mounted in the shaft for trimming off the cinchline and the free end after the ligature has been tightened.

18. The apparatus of claim 1 further comprising at least one electrode disposed adjacent the slot for cauterizing tissue.

19. The apparatus of claim 1 wherein the shaft further comprises a sleeve slidable with respect to the slot to compress tissue within the slot.

20. The apparatus of claim 1 wherein the shaft comprises a removable cartridge mounted at its distal end, the cartridge including the slot and the first suture.

21. Ligating apparatus comprising:
   a shaft having a distal end, a proximal end, and a slot near the distal end in which tissue may be positioned;
   a first suture detachably mounted at the distal end, the suture having a free end disposed on a first side of the slot, a knotted loop disposed on a second side of the slot opposite the free end and a cinching line extending proximally from the knotted loop;
   means on the shaft for threading the free end through the knotted loop while tissue is positioned in the slot such that the suture forms a ligature surrounding the tissue;
   a first rod slidably mounted in the shaft for pulling the free end axially relative to the shaft to tighten the ligature; and
   an actuator connected to the cinching line and slidably coupled to the shaft at the proximal end, wherein proximal translation of the actuator draws the cinchline to tighten the knot.

22. The apparatus of claim 21 wherein the threading means comprises a snap fitting mounted to a distal end of the rod and extending through the knotted loop, the suture further comprising a snap attached to the free end for coupling to the snap fitting, wherein the snap fitting engages the snap when the rod is moved distally and the free end is drawn through the knotted loop when the rod is moved proximally.

23. The apparatus of claim 21 wherein the suture further comprises anchor means attached to the free end.

24. The apparatus of claim 23 wherein the means for threading comprises a hook at a distal end of the rod and extending through the knotted loop, the hook engaging the anchor means when the rod is moved distally and drawing the free end through the knotted loop when the rod is moved proximally.

25. The apparatus of claim 24 wherein the anchor means comprises a ball fixed to the free end.

26. The apparatus of claim 24 wherein the anchor means comprises a knot tied in the free end.

27. The apparatus of claim 21 wherein the means for threading comprises a movable jaw forming one side of the slot, the jaw having a proximal end pivotally coupled to the shaft and a distal end on which the free end of the suture is disposed, the knotted loop being disposed on the shaft opposite the free end, whereby closure of the jaw toward the shaft threads the free end through the knotted loop.

28. The apparatus of claim 27 wherein the suture further comprises anchor means attached to the free end.

29. The apparatus of claim 28 wherein the rod has a hook at a distal end thereof for engaging the anchor means when the rod is moved distally.

30. The apparatus of claim 29 wherein the anchor means comprises a ball fixed to the free end.

31. The apparatus of claim 21 further comprising:
   a second suture detachably secured to the shaft generally parallel to the first suture and spaced apart therefrom, the second suture having a second free end on the first side of the slot, a second knotted loop on the second side of the slot and a second cinchline extending proximally from the second knotted loop and attached to the actuator;
   means on the shaft for threading the second free end through the second knotted loop while tissue is positioned in the slot such that the second suture surrounds the tissue; and
   a second rod slidably disposed in the shaft parallel to the first rod for pulling the second free end relative to the second knotted loop to tighten the second suture.

32. The apparatus of claim 31 further comprising a cutting blade slidably disposed in the shaft adjacent the first suture for dividing tissue.

33. The apparatus of claim 32 wherein the blade is disposed between the first and second sutures.

34. The apparatus of claim 32 wherein the first and second sutures are disposed on the same side of the blade.

35. The apparatus of claim 32 further comprising a third suture detachably mounted to the shaft generally parallel to the first suture and a fourth suture detachably mounted to the shaft generally parallel to the second suture.

36. The apparatus of claim 35 wherein the first and third sutures are disposed on a side of the blade opposite the second and fourth sutures.

37. The apparatus of claim 32 further comprising means at the proximal end for actuating the blade.

38. The apparatus of claim 21 wherein the slot is open in a lateral direction with the first side facing proximally and the second side facing distally.

39. The apparatus of claim 38 further comprising means on the shaft for compressing tissue within the slot.

40. The apparatus of claim 39 wherein the compressing means comprises a sleeve slidably mounted to the shaft and movable with respect to the first side of the slot, the sleeve having a distal surface for compressing tissue against the first side of the slot.

41. The apparatus of claim 21 further comprising means adjacent the slot for cauterizing tissue.

42. The apparatus of claim 41 wherein the cauterizing means comprises a first electrode on the first side of the slot and a second electrode on the second side of the slot.

43. The apparatus of claim 21 further comprising a trim blade mounted in the shaft for trimming off the cinchline and the free end after the ligature is tightened.

44. The apparatus of claim 21 wherein the shaft comprises a removable cartridge mounted at its distal end, the cartridge mounted at its distal end, the cartridge including the slot and the first suture.

45. The apparatus of claim 44 wherein the first rod is slidably disposed in the cartridge and has an interconnect at its proximal end for detachably coupling to a linkage in the shaft.

46. The apparatus of claim 44 wherein the cinchline is connected to a slidable block in the cartridge, the block having an interconnector for detachably coupling to a linkage connected to the actuator.

47. Dual ligating and dividing apparatus comprising:

a shaft having a distal end, a proximal end, and a laterally-oriented slot near the distal end in which tissue may be positioned;

a pair of sutures detachably mounted at the distal end parallel to and spaced apart from one another, the sutures each having a free end disposed on a first proximally-facing side of the slot, a knotted loop disposed on a second distally-facing side of the slot and a cinching line extending proximally from the knotted loop;

a pair of rods slidably mounted in the shaft and extending through the knotted loops, the rods each having a distal end with means for retrieving the free ends and drawing the free ends through the knotted loops;

an actuator coupled to the shaft at the proximal end, the first and second cinchlines being connected to the actuator; and a blade slidably mounted to the shaft between the sutures and movable with respect to the slot for dividing tissue.

48. The apparatus of claim 47 wherein the means for retrieving comprises a snap fitting on the distal end of each rod, the sutures further comprising a snap on the free ends for coupling to the snap fitting when the rods are moved distally.

49. The apparatus of claim 48 further comprising a pair of bipolar electrodes mounted adjacent the slot for cauterizing tissue.

50. The apparatus of claim 47 further comprising a sleeve slidably mounted on the shaft and having a distal surface for compressing tissue against the first side of the slot.

51. A method of ligating a body structure, said method comprising:

providing a ligation apparatus having a shaft with a distal end and a proximal end, a rod which is axially translatable relative to the shaft, and an actuator which is separately axially translatable relative to the shaft;

positioning the apparatus such that a portion of the body structure is within a slot at the distal end of the shaft, with a free end of a first suture being disposed on one side of the slot and a knotted loop in the suture being disposed on an opposing side of the slot;

threading the free end through the knotted loop such that the suture forms a first ligature surrounding the structure;

retrieving the free end with the distal end of the rod;

tightening the first ligature tightly around the structure by sliding the rod in a proximal direction relative to the shaft; and cinching the knotted loop using the actuator, the actuator being connected to a cinchline extending proximally from the knotted loop.

52. The method of claim 51 wherein the apparatus further includes a second suture disposed at the distal end of the shaft generally parallel to the first suture and spaced apart therefrom, the second suture having a second free end and a second knotted loop on opposing sides of the slot, the method further comprising:

threading the second free end through the second knotted loop such that the second suture forms a second ligature surrounding the structure;

retrieving the second free end with the distal end of a second rod slidably disposed in the shaft;

tightening the second suture around the structure by sliding the second rod in a proximal direction; and cinching the second knotted loop using the actuator, the second suture having a second cinchline extending from the second knotted loop to the actuator.

53. The method of claim 52 further comprising dividing the body structure between the first and second sutures after the steps of tightening the first and second knotted loops.

54. The method of claim 53 further comprising compressing the tissue in the slot.

55. The method of claim 54 further comprising cauterizing tissue in the slot by means of electrodes mounted adjacent the slot.

56. The method of claim 51 wherein the rod has a snap fitting at its distal end, and the free end has a snap fixed thereto, the step of retrieving comprising advancing the rod in a distal direction toward the free end to engage the snap in the snap fitting.

57. The method of claim 56 wherein the rod extends through the knotted loop, the step of threading comprising engaging the snap on the free end with the snap fitting on the rod and sliding the rod in a proximal direction to pull the free end through the knotted loop.

58. The method of claim 51 wherein the rod has a hook at its distal end, and the free end has an anchor fixed thereto, the step of retrieving comprising advancing the rod in a distal direction toward the free end to engage the anchor in the hook.

59. The method of claim 58 wherein the rod extends through the knotted loop, the step of threading comprising snaring the anchor with the hook and sliding the rod in a proximal direction to pull the free end through the knotted loop.

60. The method of claim 51 wherein the free end is disposed at a distal end of a movable jaw pivotally coupled to the shaft to form a side of the slot, the knotted loop being disposed on the shaft opposite the free end, the step of threading comprising closing the jaw to pass the free end through the knotted loop.

61. Ligating apparatus comprising:

a shaft having a proximal end and a distal end;

a length of suture having a proximal end, a distal end, and a knotted loop in the suture spaced proximally from the distal end;

means near the distal end of the shaft for detachably supporting the distal end of the suture and the knotted loop in a spaced-apart configuration to define a receiving space therebetween, whereby the receiving space can be placed over a tissue structure to be ligated;

means actuable from the proximal end of the shaft for capturing the distal end of the suture and drawing said distal end through the knotted loop to form a ligature around the tissue structure; and means actuable from the proximal end of the shaft for drawing proximally on the proximal end of the suture to tighten the knotted loop onto the distal end of the suture which has been drawn therethrough.

* * * * *